(12) United States Patent
Casey et al.

(10) Patent No.: US 7,264,590 B2
(45) Date of Patent: Sep. 4, 2007

(54) REAL-TIME MEDICAL MONITORING APPLICATION WITH A NETWORK INTERFACE DEVICE

(75) Inventors: Shawn Casey, Littleton, CO (US);
Steven M. Casey, Littleton, CO (US);
Bruce A. Phillips, Erie, CO (US)

(73) Assignee: Qwest Communications International Inc., Denver, CO (US)

( * ) Notice: Subject to any disclaimer, the term of this patent is extended or adjusted under 35 U.S.C. 154(b) by 523 days.

(21) Appl. No.: 10/445,275

(22) Filed: May 23, 2003

(65) Prior Publication Data

US 2004/0153289 A1 Aug. 5, 2004

Related U.S. Application Data

(63) Continuation-in-part of application No. 10/367,597, filed on Feb. 14, 2003, and a continuation-in-part of application No. 10/356,364, filed on Jan. 31, 2003, now Pat. No. 7,180,988, and a continuation-in-part of application No. 10/356,688, filed on Jan. 31, 2003, and a continuation-in-part of application No. 10/356,338, filed on Jan. 31, 2003.

(51) Int. Cl.
*A61B 5/00* (2006.01)

(52) U.S. Cl. .................. 600/300; 379/106.1; 128/903; 128/920

(58) Field of Classification Search ........ 600/300–301; 705/2–4; 379/106.1–106.2; 128/903–905, 128/920
See application file for complete search history.

(56) References Cited

U.S. PATENT DOCUMENTS

| | | | |
|---|---|---|---|
| 5,202,765 A | 4/1993 | Lineberry | |
| 5,673,692 A * | 10/1997 | Schulze et al. | ............. 600/301 |
| 5,740,075 A | 4/1998 | Bigham et al. | |
| 5,784,683 A | 7/1998 | Sistanizadeh et al. | |
| 5,923,379 A | 7/1999 | Patterson | |
| 5,971,921 A | 10/1999 | Timbel | |
| 5,983,068 A | 11/1999 | Tomich et al. | |
| 6,209,025 B1 | 3/2001 | Bellamy | |

(Continued)

OTHER PUBLICATIONS

Frank, Edward and Holloway, Jack; "Connecting the Home with a Phone Line Network Chip Set", IEEE Micro, Mar.-Apr. 2000, pp. 2-14.

*Primary Examiner*—Max F. Hindenburg
*Assistant Examiner*—Michael C Astorino
(74) *Attorney, Agent, or Firm*—Townsend and Townsend and Crew LLP

(57) ABSTRACT

Systems and methods are provided for medical monitoring of a patient at a patient premises. A medical-data collection device is adapted to collect medical data from the patient. The medical-data collection device is interfaced with a transport medium internal to the patient premises. A network interface device is also provided with multiple application devices interfaced with the transport medium internal to the patient premises. One of the application devices is a medical-monitoring application device adapted to process the collected medical data. Another of the application devices is adapted to exchange data with a transport medium external to the patient premises. A processor in communication with the application devices is adapted to coordinate transmission of the collected medical data over the transport medium external to the patient premises.

29 Claims, 10 Drawing Sheets

U.S. PATENT DOCUMENTS

| | | |
|---|---|---|
| 6,282,189 B1 | 8/2001 | Eames |
| 6,443,890 B1 * | 9/2002 | Schulze et al. ............. 600/300 |
| 6,544,174 B2 * | 4/2003 | West et al. ................. 600/300 |
| 6,807,564 B1 * | 10/2004 | Zellner et al. .............. 600/300 |
| 2003/0026416 A1 | 2/2003 | Fusco |

* cited by examiner

REAL-TIME MEDICAL MONITORING APPLICATION WITH A NETWORK INTERFACE DEVICE

CROSS-REFERENCES TO RELATED APPLICATIONS

This application is a continuation-in-part of U.S. patent application Ser. No. 10/367,597, entitled "SYSTEMS AND METHODS FOR PROVIDING APPLICATION SERVICES VIA A NETWORK INTERFACE DEVICE," filed Feb. 14, 2003 by Steven M. Casey et al.; is a continuation-in-part application of U.S. patent application Ser. No. 10/356,364, now U.S. Pat. No. 7,180,988 B2, entitled "PACKET NETWORK INTERFACE DEVICE AND SYSTEMS AND METHODS FOR ITS USE," filed Jan. 31, 2003 by Bruce A. Phillips et al.; is a continuation-in-part application of U.S. patent application Ser. No. 10/356,688, entitled "SYSTEMS, METHODS AND APPARATUS FOR PROVIDING A PLURALITY OF TELECOMMUNICATION SERVICES," filed Jan. 31, 2003 by Bruce A. Phillips et al.; and is a continuation-in-part application of U.S. patent application Ser. No. 10/356,338, entitled "CONFIGURABLE NETWORK INTERFACE DEVICE AND SYSTEMS AND METHODS FOR ITS USE," filed Jan. 31, 2003 by Bruce A. Phillips et al., the entire disclosure of each of which is herein incorporated by reference for all purposes. These applications are sometimes referred to collectively herein as "the parent applications.

BACKGROUND OF THE INVENTION

This application relates generally to medical monitoring functions. More specifically, this application relates to medical monitoring with a network interface device.

There is currently a widespread need for individuals with health concerns to have their medical status monitored. For example, many elderly people live alone and may be unable to reach a telephone to dial an emergency number in the event of a medical emergency. Even if capable of operating a telephone, many elderly people do not wish to be tied to the immediate vicinity of a telephone in case assistance is needed. Furthermore, many individuals require that their medical status be monitored as an aid to diagnosis. It is well known that these needs are increasing as a result of an increase in the average age of populations in the United States and elsewhere.

A variety of monitoring systems have been proposed for these types of circumstances. For instance, some systems are intended only for emergency response and include transmitters operable to send signals to a receiver, which in turn initiates a telephone call to a monitoring center. Such systems typically require action on the part of an individual to initiate transmission of the signals, such as by pushing a button on the transmitter. Other systems provide monitoring of physiological parameters. For example, a cardiac halter monitor is a portable device that records cardiac rhythms over a period of about 24 hours. The halter monitor is hooked up with adherent pads to a patient's chest, who wears it home. When unusual cardiac activity is detected by the patient, a button is pushed that records the activity onto a storage unit in the monitor. The recorded information may then be downloaded when the halter monitor is returned to a medical facility, which may be inconvenient.

There is accordingly a general need in the art for improved medical monitoring systems and methods for their use.

BRIEF SUMMARY OF THE INVENTION

Embodiments of the invention make use of a network interface device for monitoring medical data, and in some instances the network interface device may also provide other functionality such as support for telecommunications applications. Generally, the network interface device is located at a patient premises and interfaces with a transport medium internal to the patient premises where the medical data are collected. In some instances, the monitoring of medical data is performed in real time while in other instances, the medical data may be stored for later retrieval.

Thus, in one set of embodiments, a system is provided for medical monitoring of a patient at a patient premises. A medical-data collection device is adapted to collect medical data from the patient. The medical-data collection device is interfaced with a transport medium internal to the patient premises. A network interface device is also provided with a plurality of application devices interfaced with the transport medium internal to the patient premises. A first of the application devices comprises a medical-monitoring application device adapted to process the collected medical data. A second of the application devices is adapted to exchange data with a transport medium external to the patient premises. A processor in communication with the plurality of application devices is adapted to coordinate transmission of the collected medical data over the transport medium external to the patient premises.

In some such embodiments, the medical-data collection device comprises a first unit interfaced with the transport medium internal to the patient premises and a second unit adapted to be carried by the patient about the patient premises. The first and second units are adapted to support wireless communication from the second unit to the first unit. In some instances, the first and second units may be further adapted to support wireless communication from the first unit to the second unit. Such wireless communication may provide for exchange of voice information. In one embodiment, the second unit comprises a portable panic device equipped to transmit a request for emergency assistance upon activation. In another embodiment, the second unit is adapted to measure physiological parameters of the patient.

The network interface device may further comprise a storage device for storing the medical data. In some instances, the transport medium external to the patient premises may comprise the Internet, in which case the processor may be adapted to authenticate a user attempting to establish a connection with the network interface device through the Internet. A third of the application devices may comprise a digital conversion application adapted to convert the collected medical data to a desired format. In one embodiment, a third of the application devices is adapted to provide telecommunications services to the patient premises.

In another set of embodiments, a method is provided for monitoring a medical status of a patient at a patient premises. Medical data are collected from the patient with a medical-data collection device. The collected medical data are transmitted over a transport medium internal to the patient premises from the medical-data collection device to a network interface device disposed external to the patient premises. The collected medical data are thereafter transmitted over a transport medium external to the patient premises to a recipient.

In some such embodiments, the collected medical data indicate a need for an emergency response, in which case a request for the emergency response is transmitted over the transport medium external to the patient premises. The need for the emergency response may be indicated with a call for the emergency response from the patient, such as by activating a panic device or through a voice request. Alternatively, the need for the emergency response may be indicated by a deviation of a physiological parameter measured from the patient from a defined range.

In other embodiments, the collected medical data define a physiological parameter measured from the patient. In some instances, the collected medical data are stored on a storage device comprised by the network interface device. In some instances a request for the collected medical data may be received from the recipient at the network interface device, in which case transmitting the collected medical data may be performed in response to the request. The recipient may be authenticated prior to transmitting the collected medical data. In one embodiment, the collected medical data are digitally converted prior to transmission. In another embodiment, a telecommunications service is also provided to the patient premises with the network interface device.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a capital-letter sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

1. Introduction

Figure 1A:
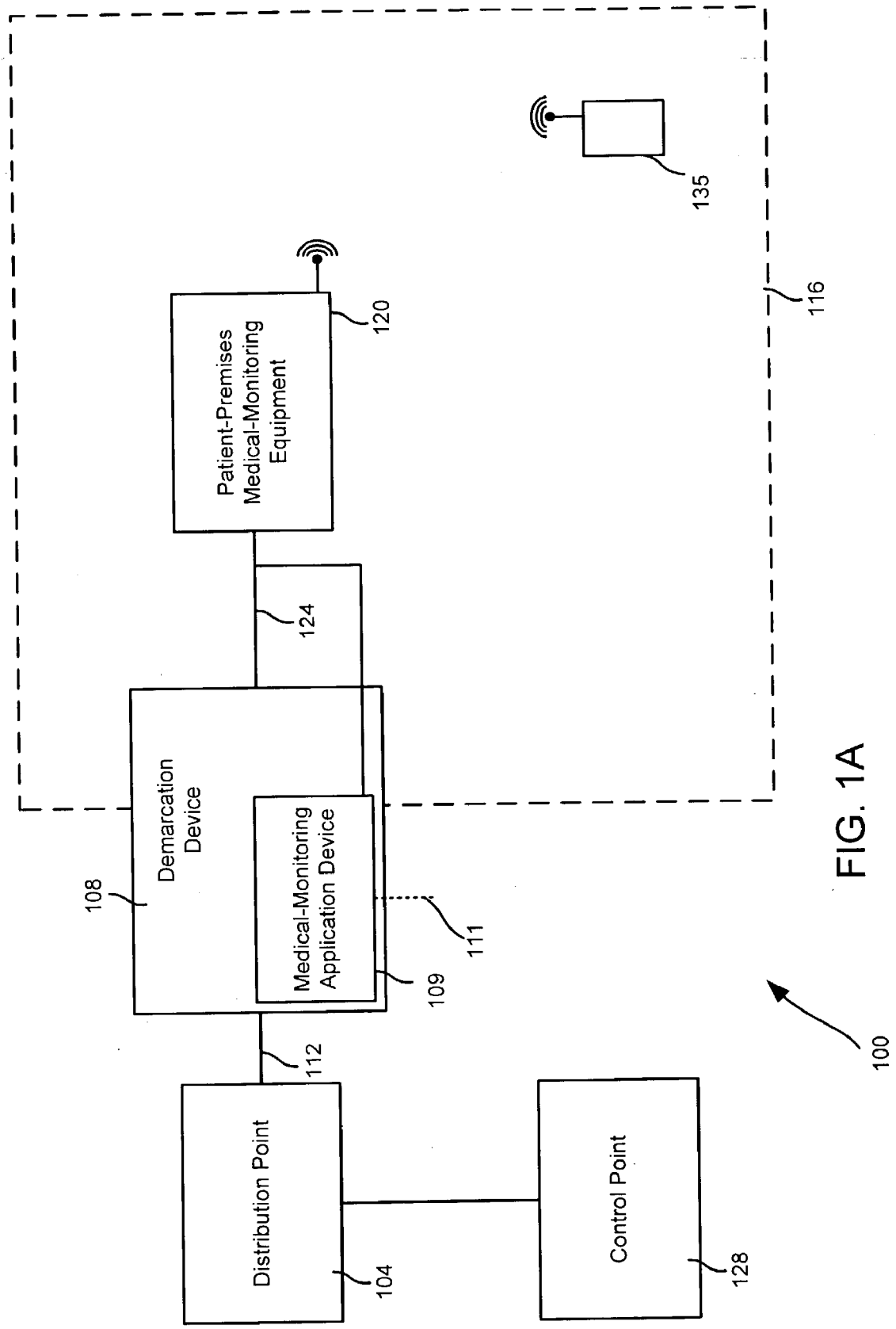
FIGS. 1A-1D provide schematic illustrations of embodiments of the invention that use demarcation and application devices to provide medical-monitoring functions with a network interface device.

Embodiments of the invention are directed to methods and systems for providing medical-monitoring services, which may in some instances be provided in real time. Some embodiments of the invention advantageously permit the medical-monitoring services conveniently to be offered in combination with other applications, the scope of which may be broad. For example, in addition to further monitoring applications, these other supplementary applications may include such application services as communications application services, informational application services, diagnostic application services, and data storage application services, among others. Several specific examples of supplementary application services that may be provided are discussed in greater detail below.

In embodiments of the invention, the medical-monitoring and other supplementary application services may be provided through the use of a network interface system that is capable of interfacing between a patient premises and a provider network. In some instances such an interfacing capability is performed by elements of a "demarcation device," and specific examples of how the demarcation capabilities arise in different embodiments of the network interface systems are discussed below. One particular demarcation device whose elements may be used to provide demarcation capabilities includes a network interface device ("NID"), described in detail below. In some instances, a demarcation device may additionally include other capabilities, including, for example, the capability to separate received information into discrete sets; the capability to process certain of the separated sets independently from other sets; and/or the capability to transmit different of the separated sets to different locations, perhaps through the use of different interfaces. Such capabilities may be provided for the medical-monitoring applications and/or for supplementary applications such as telecommunications applications.

In describing embodiments of the invention, references to a "patient" are intended to refer to an individual whose medical status is the subject of the services provided. For example, the patient may be an individual whose physiological status is monitored, whose medical status information is collected for a database, who is provided with a mechanism for initiating emergency-response services, and the like. A "customer" is intended to refer to any individual or entity that subscribes to the services provided. For example, the customer may correspond to the patient in circumstances where the patient pays for monitoring, emergency-response, or other services. In other instances, the customer may correspond to a relative or other individual who lives remote from the patient, who could, for example, be responsible for making treatment decisions on behalf of the patient. The customer may correspond to a health-care provider, hospital, or other institution that desires to collect medical-status information on the patient's behalf. In some embodiments, the customer may correspond to an health-insurance provider who collects medical-status information regarding the patient.

The services provided in accordance with embodiments of the invention are generally provided at "patient premises," which are intended to refer to physical structures under the control of the patient or other customer through ownership, leasehold, or any other property right. The term is not intended to encompass open real property external to the physical structures, even if such open real property is also under the control of the patient or other customer. Such a definition reflects differences in accessibility to the physical structures and surrounding open real property. Access to the physical structures generally requires the presence of the patient, customer, or a representative of the patient or customer, while access to the surrounding open real property may be obtained by means that does not require the physical presence of the patient or customer. Thus, for example, in the case of a residential patient, the patient premises may correspond to the patient's home, but does not include the yard surrounding the home. Access to the yard may be obtained even when the patient is not home, such as when the patient is at work, is shopping, or is otherwise unavailable to be physically present.

In this application, the term "medical-monitoring service provider" refers to any entity that provides medical-monitoring services to a patient's premises. Such medical-monitoring services may include emergency-response services, real-time diagnostic monitoring services, medical-status data-collection services, and the like. In different instances, such services may be provided at the direction of the patient or may be provided on behalf of different customers as described above.

The term "information set" is intended to describe a discrete subset of the information transmitted across a particular transport medium and/or received by a device having demarcation capabilities. Generally, the information that is classified part of a particular information set shares a common characteristic. Merely by way of example, an information set could comprise information directed specifically at medical-monitoring functions. With respect to supplementary applications, an information set could comprise telecommunication information of a particular type, such as voice, IP data, encoded video, and such; information associated with a particular supplementary application, such as information assigned to a specific IP port; information addressed to or received from a particular device or network segment; information received within a particular reception window; and the like.

In certain embodiments, demarcation capabilities can support the one-way flow of information, such as exemplified by the case of basic services in which contact of emergency personnel is initiated upon receipt by the medical-monitoring service provider of an emergency signal. In other embodiments, demarcation capabilities can support bidirectional flow of information both to and from a patient premises. In still other embodiments, the demarcation capability can support both unidirectional and bidirectional information flows simultaneously, depending on the type of information transmitted or the source of the information.

The demarcation capabilities may also function to isolate the medical-monitoring service provider's network from the network at the patient premises. As described in detail below, the network used by the medical-monitoring service provider is one example of an "external transport medium" and the patient's network is one example of an "internal transport medium." The external transport medium and internal transport medium are each examples of a "transport medium," which is used herein to describe any cable, wire, or other medium capable of carrying information, including, but not limited to, twisted pair copper wiring (shielded or unshielded, including, for example, unshielded cables complying with industry-standard categories 3, 5, 5e and 6), optical fiber, and coaxial cable. Other examples of transport media include universal serial bus ("USB") cable, cable complying with the Institute of Electrical and Electronics Engineers' ("IEEE") 1394 standard, as well as any medium capable of complying with the many local-area networking standards known in the art. The preceding are examples of transport media that comprise physical media, but the invention is not limited to the use of physical media. In other embodiments, a transport medium may comprise any of a wide variety of wireless transmissions, including infra-red transmissions, radio frequency ("RF") transmissions, and transmissions complying with standards developed by any of the IEEE's working groups governing wireless communication (e.g., the 802.11, 802.15, 802.16 and 802.20 working groups), as well as point-to-point microwave, satellite, cellular/PCS, and/or ultra wideband transmissions, among others.

In certain embodiments, demarcation capabilities can define an active demarcation point, serving to isolate the external transport medium from the internal transport medium (perhaps via an isolation device, discussed below), such that operational changes in one network do not affect the other network. "Operational changes" can include any changes in the structure, topology, format, protocol, bandwidth, media, and/or other operational parameters of a network. This isolation feature can provide many benefits; for instance, the demarcation capability can be realized by a disclosed interface between a patient premises and a provider's network, allowing the provider to implement changes in its network without disrupting the service provided to the patient or other customer.

Likewise, the isolation of the internal transport medium from the external transport medium can allow for any variety of patient-premises equipment to be used at the patient premises without fear that the equipment might be incompatible with a particular service provider's standards. The term "patient-premises equipment" is intended to refer to any device that sends, receives, or otherwise uses information in providing medical-monitoring services. Moreover, the demarcation capabilities might serve to couple a plurality of external and/or internal transport media, allowing interoperation among them all, and to provide the same isolation features among all of these media.

In this way, certain aspects of the demarcation capabilities can allow for sales of a wide variety of patient-premises equipment on a consumer electronics model, instead of the proprietary model necessitated by many of today's telecommunication networks, where, for example, differing implementations of xDSL among providers virtually force consumers to purchase modems from the providers to ensure compatibility between the modem and the provider's xDSL implementation. By isolating the topologies of the external and internal transport media, embodiments of the present invention can create a disclosed interface between the provider's network and the patient's network, allowing much greater flexibility in both the provider's networking options and the patient's choice of appliances. Those skilled in the art will recognize that these and many other benefits result from embodiments of the invention.

In accordance with other embodiments, the isolation abilities also allow insulation between different transport media coupled to the internal and external transport media in order. This may permit, for example, preventing unwanted information of one network from entering the other network. For instance, a demarcation capability of a network interface system in accordance with particular embodiments can serve to prevent propagation of certain information from an internal network (including particular signals or frequencies) into one or more external transport media, preventing interference in the internal transport medium from interfering with the medical-monitoring service provider's network. In similar fashion, demarcation capabilities can prevent the contamination of the internal transport medium with unwanted information from the external medium, interference between two or more external transport media coupled, and unwanted interference or crosstalk between multiple internal media.

In some embodiments, the isolation of the internal transport medium from the external transport medium resulting from the demarcation capabilities also allows enhanced security to be provided for the patient and/or to control patient or customer access to certain features or services. For instance, those skilled in the art will recognize that demarcation capabilities can prevent unauthorized access to the patient's data network, such as by a telecommunication service provider and/or a third party, or can screen or filter telecommunication information entering or leaving the patient's premises. This enables features such as parental controls to be placed on incoming and outgoing information, as well as filtering of outgoing sensitive information, such as credit card information and the like.

Further, according to certain embodiments, the demarcation capabilities may be used to define a consolidation point for all information entering or leaving the patient premises. Definition of such a consolidation point permits a variety of enhanced features to be provided to the entire premises, including, in addition to the medical-monitor applications, such supplementary application features as caller identification, premises-wide telephone, video and data distribution, content on demand, including video, audio, and/or data on demand, and the like. These and other supplementary features resulting from demarcation capabilities also allow for a variety of new and useful telecommunication applications to be provided in addition to the medical-monitoring applications. Specific details of some exemplary applications are discussed below; given the disclosure herein, those skilled in the art can appreciate the wide variety of such applications that are possible using various embodiments of the invention.

In a number of embodiments, the demarcation capability is applied specifically to a patient premises, thereby separating a transport medium internal to the patient premises from a transport medium external to the patient premises. Moreover, the demarcation is exploited to provide one or more addressable application devices in a configuration that permits services to be provided by the application devices to the entire premises. For example, the addressable application devices may be disposed external to the patient premises, as may be one or more processors. The addressable application devices may be adapted to interface with the transport medium internal to the patient premises, and the processors may be adapted to selectively process information originating from the transport medium external to the patient premises. Applications may be implemented through transmission of the processed information from the processors to the addressable application devices. Not only does such a configuration permit applications to service the entire premises, disposing the addressable application devices external to the patient premises makes them easily accessible by technicians as need for service or to change their operational states.

2. Organizational Configurations

There are numerous organizational configurations that may be used in accordance with embodiments of the invention. Several examples are shown schematically in FIGS. 1A-1D, although such examples are not intended to be exhaustive and further examples of organizational configurations are provided in the parent applications. A relatively simple arrangement is shown in FIG. 1A, which illustrates a configuration 100 for providing medical-monitoring services. The configuration 100 includes a distribution point 104 in communication with a device 108 having demarcation capabilities via an external transport medium 112. In this example, the external transport medium 112 comprises a transport medium external to a patient premises 116. The device 108 is shown in FIG. 1A as including a medical-monitoring application device 109, which is adapted to interface with an internal transport medium 124. In this example, the internal transport medium 124 comprises a transport medium internal to the patient premises 116. While the medical-monitoring application device 109 is shown as part of the demarcation device 108, this is not a requirement. In other instances, the medical-monitoring application device 109 may be distinct from, but coupled with, the demarcation device 108, such as by using a modular design with plug-and-play technology. Other examples discussed below illustrate different ways in which the demarcation and medical-monitoring application devices 108 and 109 may be configured as integrated or separate devices. Furthermore, additional application devices may be included with each demarcation device 108, in addition to the medical-monitoring application device 109, in other embodiments, including the application devices discussed in greater detail in the parent applications.

In one sense, the distribution point 104 may be considered to be a source of information transmitted to the patient premises and a recipient of information transmitted from the patient premises; as described below, however, the distribution point 104 need not be either the ultimate source nor the ultimate recipient of such information. In certain embodiments, the distribution point 104 may correspond to a medical-monitoring service provider's local office. In other embodiments, the distribution point may correspond to another network element in the medical-monitoring service provider's network. More generally, the distribution point 104 may correspond to any facility that is capable of transmitting information to, and/or receiving information from, a patient premises 116. In general, distribution points can be classified, inter alia, as discrete distribution points or complex distribution points. With respect to a particular information set, a discrete distribution point often transmits only the necessary or desired information to the demarcation device 108. In contrast, a complex distribution point can transmit the entire information set to the demarcation device 108. Those skilled in the art will appreciate that each scheme presents relative advantages and disadvantages.

Distribution point 104 can be capable of transmitting and/or receiving any type of information to/from the demarcation device 108, and such information can be organized into a plurality of information sets, as necessary. For ease of description, FIG. 1A does not show any additional sources or recipients of information in communication with distribution point 104, but those skilled in the art will recognize that in many embodiments distribution point 104 can be coupled to multiple patient premises 116 (perhaps via a demarcation device 108 at each patient premises) and often is neither the ultimate source nor the ultimate recipient of information. Instead, distribution point 104 usually serves as an intermediary between one or more patient premises 116 and one or more larger networks and/or providers. Further, many such networks (as well as, in some embodiments, distribution point 104) can be coupled to the Internet, so that distribution point 104 can serve as a gateway between patient premises 116 and any source and/or recipient of information that has a connection to the Internet. Examples of the utility of such configurations is discussed in further detail below.

In configuration 100, the demarcation device 108 can serve as the interface between external transport medium 112 and patient premises 116. As shown in FIG. 1A, usually both the demarcation device 108 and the medical-monitoring application device 109 are interfaced with the internal transport medium 124, with the demarcation device interfaced with the external transport medium 112, although other interfacing configurations are also within the scope of the invention. For example, the medical-monitoring application device 109 may additionally be interfaced with the external transport medium 112. The medical-monitoring application device may also include a service interface 111 for addressing the medical-monitoring application device 109. The service interface 111 may comprise a physical interface, such as a universal serial bus ("USB"), FireWire (IEEE 1394), registered jack 11 ("RJ-11"), registered jack 45 ("RJ-45"), serial, coax, or other physical interface known to those of skill in the art. In other embodiments, the service interface 111 may comprise a logical interface, such as may be provided through a logical connection with an IP address.

As conceptually illustrated in FIG. 1A, demarcation device 108 and/or medical-monitoring application device 109 may be attached to an external wall of the patient premises 116. Such attachment may be performed of an integrated demarcation device 108 or may be performed with the components separately of a separated demarcation device 108. Such a configuration provides many advantages. For instance, if the medical-monitoring service provider desires to upgrade or otherwise change its network, including, perhaps, external transport medium 112, a technician can perform any necessary changes at demarcation device 108 and/or medical-monitoring application device 109 as appropriate without entering the patient premises 116. Coupled with the ability of some demarcation devices 108 to isolate the medical-monitoring service provider's network from the patient's premises, this can allow the medical-monitoring service provider to effect substantial changes in it network without impacting or inconveniencing the customer in any respect. This could, for example, allow the medical-monitoring service provider to upgrade external transmission medium 112 from a copper twisted pair to optical fiber, without requiring any topological changes inside the patient premises 116. Of course, demarcation device 108 and/or medical-monitoring application device 109 may be located at a variety of alternative locations, either within patient premises 116 or at a facility operated by the medical-monitoring service provider. In addition, as previously noted and as discussed in further detail below, a demarcation device 108 may also be divided, with different portions situated at different locations, according to the requirements of the implementation.

The medical-monitoring application device 109 is configured so that it may communicate with patient-premises medical-monitoring equipment 120, which may be located interior to the patient premises 116 through internal transport medium 124. Such communication is used to implement applications defined by the medical-monitoring application device 109 with the patient-premises equipment 120, perhaps in accordance with information received from the distribution point 104. In addition, the demarcation device 108 may communicate directly with patient-premises equipment 120 to implement other functions.

While the internal transport medium 124 may comprise any of the media discussed above, in one embodiment it comprises existing telephone wiring in patient premises 116 and, in some embodiments, is capable of carrying voice, data and video information. For instance, as described in Edward H. Frank and Jack Holloway, "Connecting the Home with a Phone Line Network Chip Set," *IEEE Micro* (IEEE, March-April 2000), which is incorporated herein by reference, the Home Phoneline Networking Alliance ("HPNA") standards allow for simultaneous transmission of both voice information and Ethernet frames across twisted-pair copper telephone wiring. In addition to the transmission of information through the demarcation device 108, either directly from the demarcation device 108 or through the application device 109, information may be transmitted via the reverse path to the distribution point 104. Such information received at the distribution point 104 may be transmitted to an information recipient, such as a service provider. For example, such a transmission may be used to request a pay-per-view movie or the like. Alternatively, information received at the distribution point 104 may be transmitted across the Internet, as described further in connection with some exemplary applications below.

Thus, merely by way of example, the patient-premises medical monitoring equipment 120 could comprise a wireless receiver adapted to receive signals from a wireless transmitter 135. In one embodiment, the wireless transmitter 135 may comprise a portable panic device carried by the patient by hand, on a belt, on a cord around the neck, or the like. Such a panic device may include a button for activating a request for an emergency response, which the patient may activate in response to an accident, fall, or medical condition such as a suspected heart attack. In another embodiment, the wireless transmitter 135 may comprise medical-status equipment that monitors physiological functions such as pulse, respiration rate, electrical heart activity, and the like. Furthermore, in some instances, the patient premises may be equipped with one or more fixed video cameras to permit visual monitoring of conditions. Proper operation of the wireless transmitter 135, video cameras, and/or other monitoring equipment may be verified, such as with a ping test. As such medical-status data are collected, they may be transmitted to the patient-premises medical-monitoring equipment 120 for local storage or for transmission over transport media 124 and 112 to a central facility. Data received at the central facility may be presented to medical personnel for evaluation, may be stored as part of an experimental protocol, may be stored in the patient's records, and the like. If the collected data identifies a medical emergency as defined by interpretation protocols embodied in the patient-premises medical-monitoring equipment, an emergency response may be activated automatically, without the need for the patient to initiate a request for emergency response with a panic device as described above. For example, a measurement that a patient's blood pressure exceeds a threshold level or that certain electrical heart activity is abnormal may trigger an alert. In some embodiments, an alert may be triggered by a loss of signal.

In a further embodiment, the patient-premises medical monitoring equipment 120 and the wireless transmitter 135 could both be equipped for wireless transmission and reception. For example, such capabilities could be used to support voice communications between the patient and an operator at a central facility, with transmissions over transport media 124 and 112 being coordinated with the patient-premises medical-monitoring equipment 120 and the medical-monitoring application device 109. The resulting voice-interaction capability permits the patient to provide real-time descriptions of symptoms and to receive real-time advice from the central authority. In instances where this capability is combined with an ability of the wireless transmitter 135 to collect and transmit medical-status data, the rapid diagnosis of conditions and communication of advice to the patient may benefit from the combination of real-time collected medical-status data and direct voice interaction with the patient.

In some embodiments, maintenance systems are provided to ensure that sufficient battery life is provided to the transmitters 135 or other monitoring equipment, and that sufficient signal strength is provided to permit the transmitters 135 to be moved around the patient premises without loss of signal. Such support functions could be provided with the demarcation device 108 at the patient premises, although in other embodiments monitoring of such maintenance functions could alternatively be performed at the medical-monitoring service provider.

In certain embodiments, the demarcation device 108 can receive state information from a control point 128, which is shown in the illustrated embodiment as associated with distribution point 104. In certain instances, control point 128 can be software and/or hardware operated by a medical monitoring service provider for controlling certain features of the operation of the demarcation device 108. For instance, control point 128 can instruct the demarcation device 108 to provide (or cease to provide) particular applications and/or services with the medical monitoring application device 109 to the patient premises 116. Control point 128 can also provide other directions to the demarcation device 108, including, for instance, instructions to save or record a particular information set such that the information set may be transmitted to patient premises 116, allowing the provision of updated or other relevant medical information. In some instances, the manner in which the patient-premises medical-monitoring equipment responds to certain data, e.g. to identify whether certain conditions require a critical or emergency response, may be updated to reflect new medical standards or to reflect specific characteristics of the patient's condition.

Often, it may be beneficial to allow the patient to provide state information to the demarcation device 108. Merely by way of example, such state information could define different levels of monitoring service that are to be maintained, perhaps depending on a cost that the patient or health-insurance provider is willing to pay under given circumstances. Thus, in certain embodiments, control point 128 may have a web interface, such that the customer or any authorized person, such as an employee of the medical-monitoring service provider, may log onto the web interface and configure options for the demarcation device 108, perhaps resulting in state commands being transmitted from the distribution point 104 to the demarcation device 108. In other embodiments, control point 128 can be a web interface to the demarcation device 108 itself, allowing the patient or other authorized person to configure the demarcation device 108 directly. In still other embodiments, control point 128 can communicate with the demarcation device 108 through an application programming interface ("API"). Hence, in some embodiments, control point 128 can interface with the demarcation device 108 through an API.

In many such embodiments, the API corresponds to the service interface 111 of the medical-monitoring application device 109. In embodiments where the service interface 111 comprises a logical interface, the API can include a set of software, hardware, or firmware routines or libraries that may be invoked programmatically to configure or relay information to the medical-monitoring application device 109. In that sense, then, control point 128 can be understood to be a program running on a computer, perhaps located at distribution point 104 or patient premises 116, among other locations, that provides state information to the medical-monitoring application device 109 via a software API.

In other embodiments where the service interface 111 comprises a physical interface such as those described above, the API may be accessed locally, such as by a service technician. For example, the service technician could visit property outside the patient premises 116, attach a laptop computer or other device to the physical service interface 111, and upload information to the medical-monitoring application device 109, including perhaps both state information, as well as other information. In still other embodiments, the application device 109 can accept state information through other means, including, for example, through a web interface by receiving a specially formatted electronic message. This is especially the case in embodiments where the medical-monitoring application device 109 is capable of acting as a web server, as discussed below.

The addressability of the medical-monitoring application device 109 may be used in various embodiments to change the state of the application device 109. Such state information can include instructions to modify one or more security settings of the demarcation device 108. Merely by way of example, in certain embodiments, the demarcation device 108 can include a computer virus scanner, and state information can include updated virus definitions and/or heuristics. Likewise, the demarcation device 108 often will be configured with access controls, such as to prevent unauthorized access through the demarcation device 108 by third parties. State information can include instructions on how to deal with particular third-party attempts to access the demarcation device 108 or internal transport medium 124. Those skilled in the art will recognize as well that some security settings may specify the level of access the customer has to the functions of the demarcation device 108, such as to prevent unauthorized use of certain telecommunication services, and that these settings also may be modified by received state information.

There are a variety of ways in which the various access-control and security functionalities of the demarcation device 108 discussed above may be implemented. In different embodiments, these functionalities may be performed by the demarcation device 108, by the medical-monitoring application device 109, by a combination of the demarcation and medical-monitoring application devices 108 and 109, and/or by still other components that may additionally be comprised by the demarcation device 108. Moreover, the state information that manages such functionalities may sometimes be sent periodically to the demarcation device 108 to ensure that it is current.

Figure 1B:
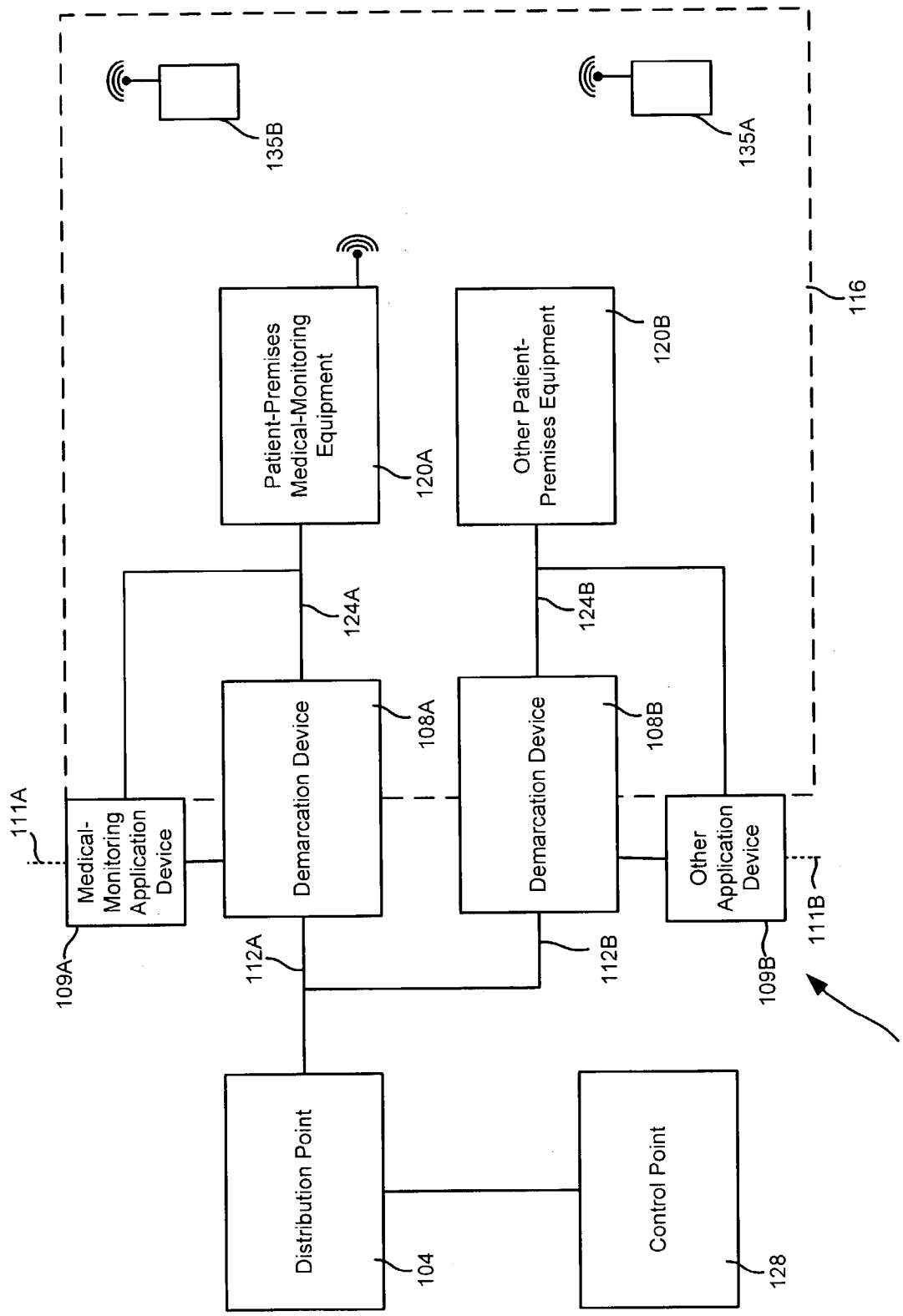

Turning now to FIG. 1B, configuration 100' is illustrative of certain embodiments that can provide multiple demarcation devices 108 at patient premises 116. A first demarcation device 108A comprises demarcation device 108A and medical-monitoring application device 109A, and a second demarcation device 108B comprises demarcation device 108B and another application device 109B. The other application device 109B may be configured to provide other application services to the patient premises, such as a variety of different telecommunications services and other services described in detail in the parent applications. In illustration of FIG. 1B, both the medical-monitoring and other application devices 109 are shown as separated from the respective demarcation devices 108, although one or more of the multiple demarcation devices 108 may alternatively comprise structures in which they are integrated. In instances where the demarcation devices 108 have separated demarcation-and application-device components, the separate components may both be affixed to an exterior wall of the patient premises 116. This has the same advantages discussed previously in connection with integrated demarcation devices, namely ease of upgrading or otherwise changing the network by a service provider. In other instances, the separate components may be provided in different locations, such as by providing the demarcation device 108 at a facility operated by the service provider while keeping the medical-monitoring and/or other application device 109 on the exterior wall of the patient premises 116.

Similar to the configuration of FIG. 1A, the medical-monitoring application device 109A may be in communication with patient-premises equipment 120A through internal transport medium 124A and application device 109B may be in communication with patient-premises equipment 120B through internal transport medium 124B. Implementation of the medical-monitoring and other applications provided by application devices 109A and 109B can thus be achieved respectively with information received and transmitted by demarcation devices 108A and 108B. In addition, demarcation device 108A can be in direct communication with patient-premises equipment 120A through internal transport medium 124A, and demarcation device 108B can likewise be in direct communication with patient-premises equipment 120B through internal transport medium 124B. Each of the demarcation devices 108 may be provided in communication with a common distribution point 104 through their respective demarcation devices 108. In particular, demarcation device 108B can communicate with distribution point 104 through external transport medium 112B which, as illustrated by FIG. 1B, can simply be spliced into external transport medium 112A, such as by using an active or passive splitting device, which could be optical, as in a fiber environment, or electrical. If desired, demarcation devices 108 and/or distribution point 104 can include control logic to prevent unauthorized access by demarcation device 108A to telecommunication information sent to or received from demarcation device 108B, and vice versa. In other embodiments, external transport medium 112B could run directly from demarcation device 108B to distribution point 104. In still other embodiments, external transport medium 112B could be omitted, with demarcation device 108B coupled to demarcation device 108A, which could then provide connectivity between demarcation device 108B and distribution point 104 through external transport medium 112A.

Configuration 100' can be used in a variety of implementations. For instance, if patient premises 116 is a multiple-dwelling unit of which only some dwellings require medical-monitoring services, separate demarcation devices 108 can be provided for each separate resident or family. If there are multiple dwellings that require medical monitoring services, a single demarcation device, perhaps with more interfaces, could service multiple those units. In such implementations, especially when external transport medium 112B does not directly couple demarcation device 108B to distribution point 104, demarcation devices 108A, 108B can include security functionality, for example to prevent signals intended for patient-premises equipment 120A from reaching patient-premises equipment 120B and vice versa. In some embodiments, demarcation devices 108 can provide a variety of such security, encryption, and authentication functions.

Figure 2A:
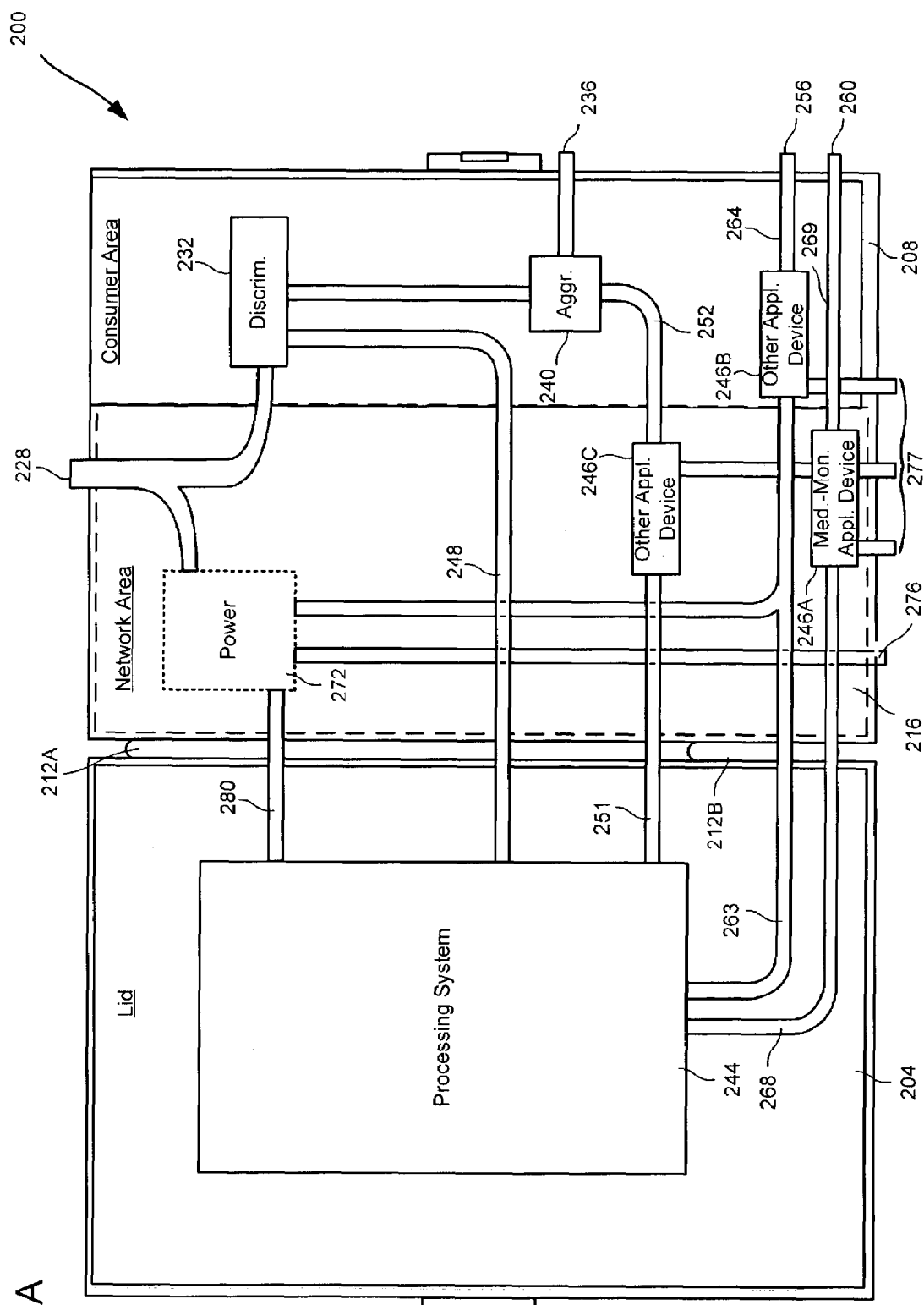
FIGS. 2A-2C provide schematic illustrations of network interface devices that provide medical-monitoring applications according to embodiments of the invention.

The description above provides a specific example of a more general class of embodiments in which multiple demarcation devices 108 are daisy-chained together, using any of the media discussed herein. This allows a service provider to provide service to additional customers without requiring any additional external transport media. Similarly, demarcation devices 108 at multiple premises can be coupled together, such that if the external transport medium coupled to one of the demarcation devices 108 fails, that device can maintain connectivity to the distribution point through its connection to another demarcation device 108. A demarcation device 108 in accordance with specific embodiments thus may have an interface for securely connecting to one or more additional demarcation devices 108, and thus forming a mesh network of demarcation devices and/or distribution points. This allows a particular demarcation device 108 to serve as a conduit between another interface device and a distribution point without allowing any unauthorized reception of telecommunication information intended for the connected interface device. This secure interface can be included, for instance, in a portion of the demarcation device 108 that is inaccessible to customers, as illustrated in FIG. 2A and described below.

FIG. 1B also illustrates that multiple wireless transmitters 135A and 135B may be used in conjunction with a single set of patient-premises medical-monitoring equipment 120A. Each of the wireless transmitters 135A and 135B may use different frequency or modulation characteristics to distinguish themselves in communications with the patient-premises medical-monitoring equipment. Each wireless transmitter 135 may correspond to one of the devices described above, and the accommodation of multiple such devices enables a variety of applications. For instance, in the embodiment where the patient premises 116 comprises a multiple-dwelling unit, the wireless transmitters 135 could be distributed within the individual dwelling units that require medical-monitoring services. While all of the wireless transmitters 135 could be functionally equivalent, this is not a requirement and transmitters 135 with different functionality could be provided. This different functionality may, in some instances, be dependent on contracted service levels. For example, in one dwelling unit, a panic device could be provided while, in another dwelling unit, equipment that monitors physiological functions could be provided. Such diversity of functionality may even be provided within a single dwelling unit, either within a multiple dwelling unit or in a single-unit patient premises 116. For example, different individuals within the single unit might use different medical-monitoring equipment or a single individual might use different equipment at different times.

Figure 1C:
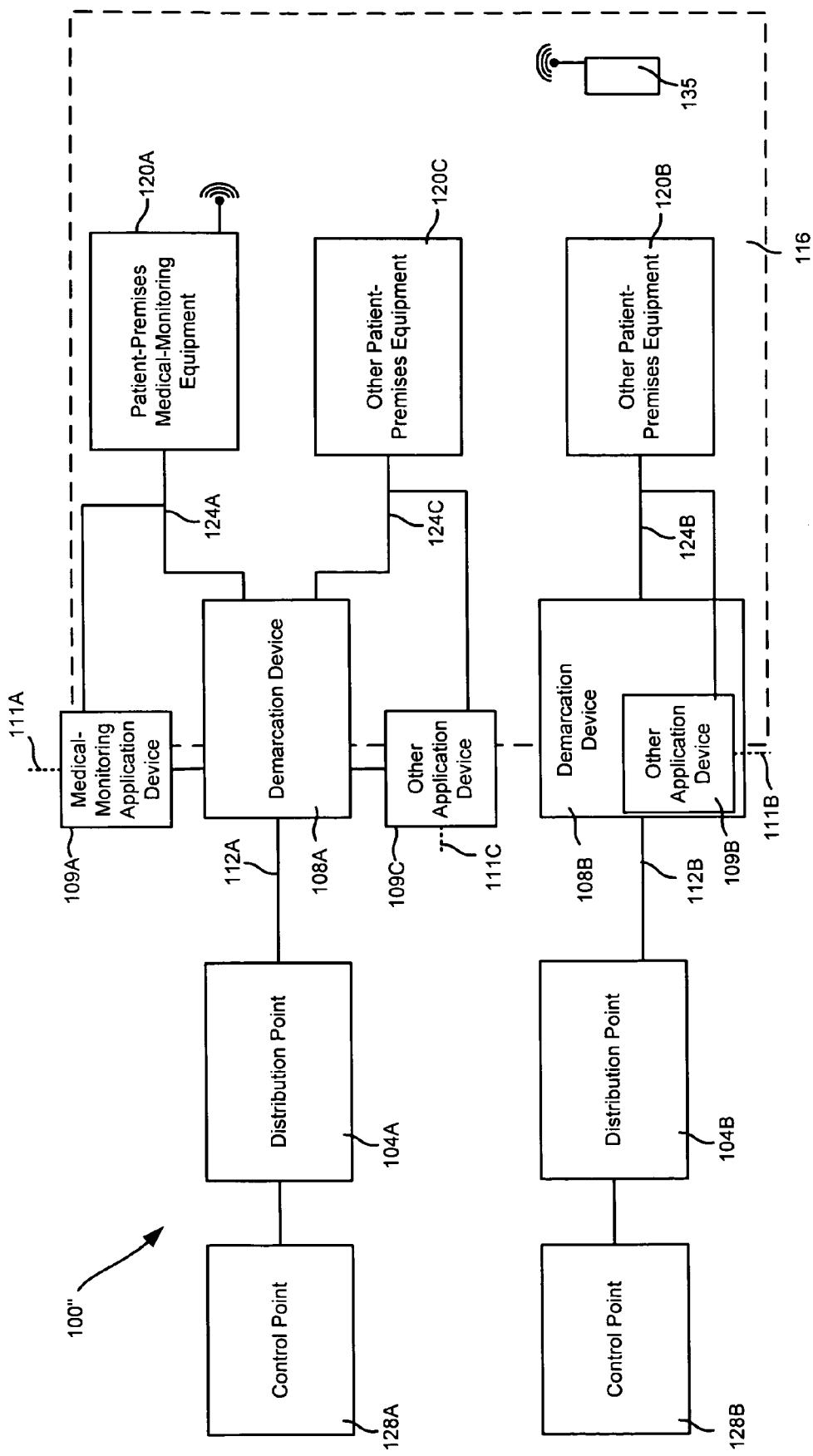

In other embodiments, a single patient premises 116 might have connections to a plurality of service providers. For example, turning now to FIG. 1C, configuration 100" includes a distribution point 104A coupled to a first demarcation device 108A via external transport medium 112A and also includes a second distribution point 104B coupled to a second demarcation device 108B via external transport medium 112B. Merely by way of example, distribution point 104B could, for example, be associated with a cable television provider, while distribution point 104A is associated with a medical-monitoring service provider. In addition, configuration 100"0 illustrates that multiple patient-premises equipment 120A and 120C may be coupled with a single demarcation device 108A. This may be done with multiple internal transport media 124A and 124C as illustrated by FIG. 1C, or may alternatively be done through a common internal transport medium as discussed below. Thus, for example, patient-premises equipment 120A could comprise wireless-receiver equipment for interacting with a wireless transmitter 135 as described above, patient-premises equipment 120C could be a modem attached to a personal computer for maintaining health-record information, and patient-premises equipment 120B could be a television whose use is unrelated to the medical-monitoring functions.

FIG. 1C further provides an example of combinations of different configurations for the demarcation devices 108. In particular, the second demarcation device 108B, connected with distribution point 104B, is shown having an integrated demarcation device 108B and application device 109B, with service interface 111B. The first demarcation device 108A, connected with distribution point 104A, is instead shown having separated demarcation and application devices.

Moreover, the first demarcation device 108A illustrates a demarcation device that may have a plurality of application devices 109A and 109C in communication with a single demarcation device 108A. Each of these application devices 109A may have a respective service interface 111A and 111C, and may be connected with different internal transport media 124A or 124C to reflect the different application capabilities. Such an arrangement could, for example, be used in embodiments where the medical-monitoring service provider also offers other services, with coordination of those multiple services being effected with the multiple application devices. Medical-monitoring application device 109A could provide the medical-monitoring functions while application device 109C provides Internet-access functions for a modem and personal computer comprised by patient-premises equipment 120C. The application device 109B comprised by the second demarcation device 108B could provide an application intended for cable-TV functions, such as a digital recorder function.

Figure 1D:
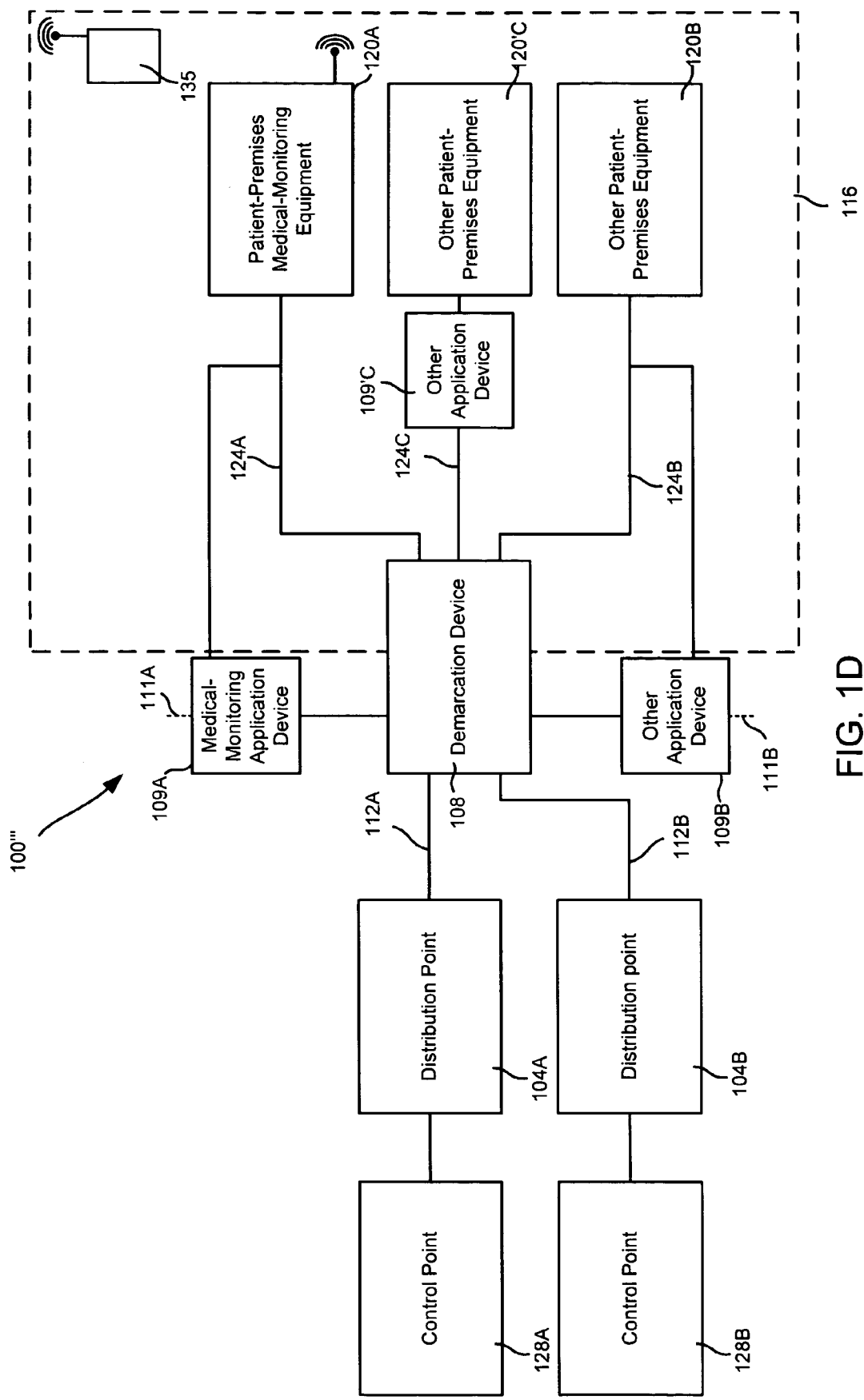

In another alternative embodiment, such as configuration 100''' illustrated in FIG. 1D, a demarcation device 108 can provide connectivity to a plurality of distribution points 104A and 104B, as well to a plurality of patient-premises equipment 120A, 120B, and 120C. In the illustrated configuration 100''', the demarcation device 108 is provided in a separated form with three application devices. The medical-monitoring application device 109A and another of the application devices 109B are provided external to the patient premises 116 and have service interfaces 111A and 111B. The third application interface 109C is provide interior to the patient premises, illustrating that it is not a requirement that all of the application devices 109 comprised by the demarcation device 108 be disposed external to the patient premises. The connectivity of a single demarcation device 108 to a plurality of distribution points 104A and 104B and to a plurality of patient-premises equipment 120A, 120B, and 120C may be effected through attachments for multiple internal transport media 124A, 124B, and 124C and for multiple external transport media 112A and 112B. One or more of the patient-premises equipment, say 120A, may comprise medical-monitoring equipment having a wireless receiver for receiving information from a wireless transmitter 135. The wireless transmitter 135 may itself comprise any of the different types of devices, some of which were described above, used in combination with the patient-premises medical-monitoring equipment 120A. Moreover, as illustrated by FIG. 1D, each distribution point 104A and 104B may be associated with a different control point 128A and 128B, respectively. In alternative embodiments, a single control point 128 could provide configuration information to the demarcation device 108 with respect to both distribution points 104A and 104B.

2. Structure of a Medical-Monitoring-Application Network Interface Device

Figure 2B:
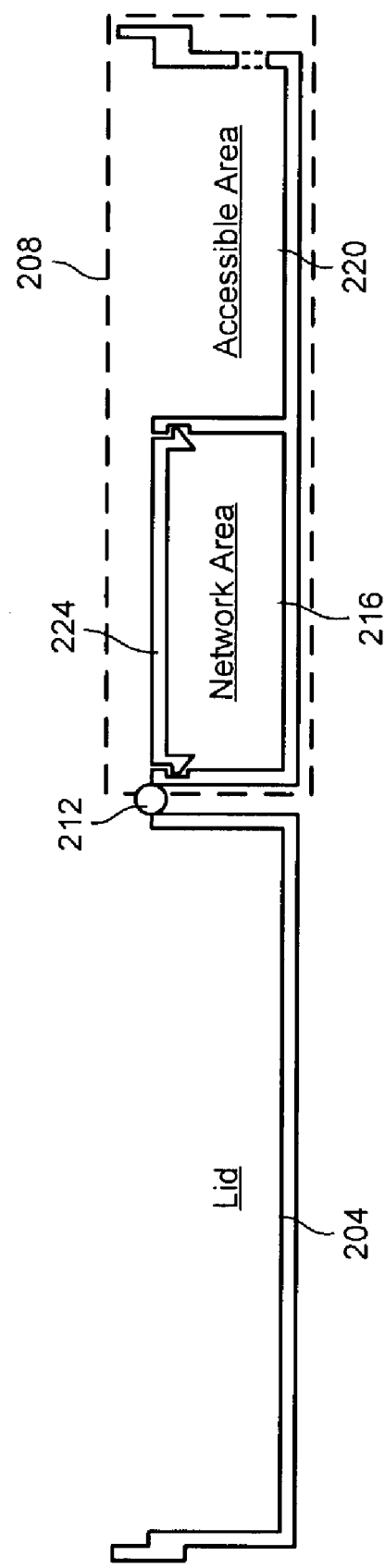

One exemplary embodiment of a network interface device 200 equipped to implement medical-monitoring applications by incorporating the demarcation and application functionality described above is illustrated in FIGS. 2A and 2B. For purposes of illustration, FIG. 2A provides a top view that explicitly shows components within the network interface device 200, while FIG. 2B provides a side view that shows the logical organization of the network interface device 200 without the components. In the illustrated embodiment, network interface device 200 comprises a clamshell design, with a lid portion 204 and a body portion 208 connected by hinges 212A and 212B. The body portion 208 comprises a network area 216 and an accessible area 220. Generally, network area 216 is adapted to receive a cover and is designed generally to be accessible only to personnel authorized by the service provider. In contrast, when network interface device 200 is open, the accessible area 220 may be accessed to add or remove components as desired. In this and other ways, the network interface device 200 serves to isolate the service provider's network from the patient's network, as described above.

The network interface device 200 can include a first interface 228 for communicating with the provider's external transport medium. Those skilled in the art will recognize that, in some embodiments, as described above, the external transport medium may comprise the twisted-pair copper "local loop" running from the patient's premises to the service provider's local office, and interface 228 will allow for the attachment of the local loop to the network interface device 200. As discussed above, in other embodiments, the external transport medium can be any of a variety of other media, including satellite transmissions, wireless transmissions, coaxial cable. In fact, in certain embodiments, the external transport medium can comprise multiple transport media (of the same or different types), for which the network interface device 200 could include multiple interfaces. In some such embodiments, the network interface device 200 can function to couple a plurality of external transport media to one another, seamlessly increasing the bandwidth available to the patient premises. For instance, a patient premises might have a satellite link to one service provider and an ADSL link to another provider, and the network interface device 200 could combine or multiplex these two links. Similarly, those skilled in the art will recognize that in certain of these embodiments, a particular external transport medium, such as a satellite link, may be more well-suited to one way transmission of information; in such cases, the network interface device 200 could use a second external transport medium, such as an ADSL link, to allow transmission in the other direction.

Interface 228 can be coupled to a discrimination device 232, which can be operative to separate information sets received on interface 228, and, conversely, aggregate information sets for transmission on interface 248. Merely by way of example, in particular embodiments, discrimination device 232 can separate POTS information from other information and/or isolate signals on the internal transport medium from the external transport medium and vice versa. In some embodiments, for instance xDSL implementations, discrimination device 232 can comprise one or more filters. Such filters can include, but are not limited to, high-pass, low-pass, and/or band-pass filters. For instance, in an xDSL implementation, discrimination device 232 might include a high-pass and/or low-pass filter for separating high-frequency (e.g., data) from low frequency (e.g., POTS) information. In other embodiments, discrimination device 232 can comprise many other types of filters, including both digital and analog filters. Discrimination device 232 can be operable to separate information sets through a variety of criteria, including for example, by frequency, by destination device, information type, and/or frequency. Further, in certain embodiments, information sets can be multiplexed (for instance, using various time-division multiplexing or wave-division multiplexing schemes known in the art) for transmission over an external transport medium, and discrimination device 232 can comprise a demultiplexer capable of separating multiplexed signals and, optionally, routing each signal to the necessary destination.

In the illustrated embodiment, discrimination device 232 is in communication with a second interface 236, which can interface with the telephone wires at the patient premises to provide traditional analog telephone service. In some embodiments, an aggregator 240 can be situated between discrimination device 232 and interface 236 to allow additional, perhaps non-POTS, information sets to be sent and received through interface 236 simultaneously with the POTS information. This can include, for example, aggregating information sets for transmission of an HPNA signal over an internal transport medium.

The discrimination device can also be coupled to a processing system 244, which in the illustrated embodiment is located in the lid portion 204, and all non-POTS information sets can be routed to processing system 244 for additional processing. Processing system 244 is described in detail below, but can, in general, comprise one or microprocessors, including digital signal processor ("DSP") chips, memory devices, including both volatile and nonvolatile memories, and storage devices, including hard disk drives, optical drives and other media. In fact, processing system 244 can comprise the equivalent of one or more personal computers, running any of a variety of operating systems, including variants of Microsoft's Windows™ operating system, as well as various flavors of the UNIX™ operating system, including open source implementations such as the several Linux™ and FreeBSD™ operating systems.

Information or information sets can be processed by processing system 244 in a variety of ways, including, for example, routing a given information set to a particular interface, transforming information such as by encoding and/or decoding information and converting between different transport protocols, storing information, filtering information, and any of the other functions described herein with respect to processing systems. In certain embodiments, processing system 244 can serve as the termination point for an external transport medium; for instance processing system 244 can incorporate the functionality of an xDSL modem. In other embodiments, processing system 244 can serve to identify quality-of-service requirements (for instance, latency requirements for voice transmissions and bandwidth requirements for streaming media transmissions, to name a few) and enforce those requirements, ensuring that sufficient bandwidth is provided to a particular device, network segment or application to maintain the quality of service required.

In certain embodiments, such as those described above with respect to FIG. 1D, a demarcation device may comprise another interface in communication with a second distribution point 104B through an additional external transport medium 112A, perhaps operated by a different service provider. In such a case, the additional external interface could be coupled to discrimination device 232, or it could be coupled to another discrimination device, which could also be in communication with processing system 244, interface 236 and/or aggregator 240. Thus, certain embodiments allow a single demarcation device to serve as a communication gateway between the patient premises and multiple service providers, including combining or multiplexing multiple external transport media, each of which may be in communication with a different service provider as discussed above.

In the illustrated example, processing system 244 is in communication with aggregator 240, which, as discussed above, can aggregate non-POTS information sets received from processing system 244 and POTS information sets received directly from discrimination device 232 for consolidated transmission via interface 236. In effect, discrimination device 232 and aggregator 240, perhaps in conjunction with processing system 244, can function to separate information received on interface 228 into a set of POTS information and a set of non-POTS information. The non-POTS information is routed via transport medium 248 to processing system 244 for processing, and the POTS information is routed to interface 236 for transmission to the internal transport medium. In certain embodiments, one or more sets of non-POTS information can be routed to interface 236 using transport medium 252 for transmission through interface 236, perhaps in combination with one or more sets of POTS information.

Of course, discrimination device 232 and aggregator 240 can perform the same function in reverse, i.e., to separate and recombine different sets of information received on interface 236 from the patient's premises. Thus, in some embodiments, both discrimination device 232 and aggregator 240 each can perform a combined discrimination-device-aggregator function, depending on the direction of information flow. In fact, while termed "discrimination device" and "aggregator" for ease of description, those two devices can actually be identical, and further, their functionality can, in some embodiments, be incorporated into a single device, which could be coupled to interface 228, interface 236, and processing system 244, and could route information sets among any of those three components as necessary. Moreover, as described below, the functionality of discrimination device 232 and/or aggregator 240 can be incorporated into processing system 244; likewise discrimination device 232 can incorporate interface 228 and/or aggregator 240 can incorporate interface 236, such that discrimination device 232 and/or aggregator 240 comprise the necessary components to be coupled directly to the external and internal transport media, respectively.

Discrimination device 232 and/or aggregator 240 can also serve another function in certain embodiments: Since the external transport medium is coupled to first interface 228 and the internal transport medium can be coupled to, inter alia, second interface 236, the discrimination device 232 and/or aggregator 240 can serve as an isolation device for intermediating between the two media, such that when a topological change occurs in one of the media, only the demarcation device interface need be changed, and the other transport medium is not affected. In some such embodiments, discrimination device 232 and/or aggregator 240 can serve to intermediate (including protocol translation and the like) between interfaces 232, 240, allowing either the internal or the external transport medium to be upgraded or changed without impacting the other transport medium. Of course, in certain embodiments, this isolation function also could be performed by processing system 244. In yet other embodiments, the isolation device might comprise a separate piece of hardware in communication with discrimination device 232, aggregator 240 and/or processing system 244.

The network interface device 200 also comprises one or more application devices 246, one of which is the medical-monitoring application device 246A. The application devices 246 are generally provided in communication with the processing system 244 by transport media 251, 263, and/or 268. In some instances, such as illustrated with the medical-monitoring application device 246A and other application device 246B, the application devices 246 may be in communication with interfaces 256 and 260 that allow communication with transport media internal to the patient premises, such as over transport media 264 and 269. For example, interface 256 could be a coaxial interface for connection to RG6 and/or RG59 cable, and interface 260 could be an RJ45 and/or RJ11 interface for connection to unshielded twisted pair cable, which can, for instance, form a 10Base-T Ethernet network.

In other instances, such as illustrated with other application device 246C, information might be routed from the application device 246C through the aggregator. Such an application may be suitable for applications that combine other applications with the medical-monitoring application and use IP data, such as a VoIP application. For example, the network interface device 200 might receive IP data, perhaps combined with other types of information, on interface 228. The information set comprising the IP data can be routed by the discrimination device 232 via medium 248 to processing system 244, where it can be processed. Depending on the embodiment, it could then be routed via transport medium 251 to VoIP application device 246C and then provided to the customer's existing telephone wiring using interface 236, optionally in conjunction with aggregator 240 and/or one or more line drivers. It could alternatively be routed to any of the other application devices 246A or 246B depending on their functionality. In this way, the demarcation device can allow virtually unlimited connectivity options for equipment at the patient premises. Adding to the flexibility of network interface device 200, the processing system 244 could include components to serve, for example, as a cable or xDSL modem, as well as components to serve as an Ethernet hub, switch, router, or gateway, the functions of each of which are familiar to those of skill in the art.

Furthermore, the application devices 246 may be provided generally within the network area 216 or in the accessible area 208, or with some in the network area 216 and others in the accessible area 208, depending on the embodiment. This is illustrated in FIG. 2A by showing the medical-monitoring application device 246A and one of the other application devices 246C disposed within the network area 216 of the network interface device 200 and the other application device 246B disposed within the accessible area 208 of the network interface device 200.

Each of the medical-monitoring and other application devices 246 may include a service interface 277 to permit states of the medical-monitoring or other application devices 246 to be changed and/or updated. As previously noted, such interfaces may comprise physical interfaces such as USB, FireWire (IEEE 1394), RJ-11, RJ-45, serial, coaxial, or other physical interfaces, to permit a service technician to interact with the medical-monitoring or other application devices 246 while at the site of the network interface device 200. Alternatively, the service interfaces 277 may comprise logical interfaces to permit IP addressing to be used in changing the state of the application devices. In many instances, the network interface device 200 may also include a future-application device with open architecture to support new applications. The architecture may be configured by use of the service interfaces 277 when the new application is implemented.

In certain embodiments, network interface device 200 can comprise a line driver (not shown on FIG. 2A or 2B), coupled to processing system 244 and aggregator 240. The line driver can function to allow conversion between various network formats and media, allowing a variety of different media types, e.g., twisted pair and/or coaxial cable, in accordance with the HPNA and HPNA+ standards, as well, perhaps, as the patient premises' A/C wiring, in accordance, for example, with the HomePlug™ standard, to transport combined POTS and non-POTS information sets.

In certain embodiments, network interface device 200 can comprise a power supply 272 for providing electrical power to the components in network interface device 200. Power supply 272 can be powered through electrical current carried on the external transport medium and received on interface 228. Alternatively, power supply 272 can receive electrical current from a coaxial interface, such as interface 256, or through a dedicated transformer plugged into an AC outlet at patient premises, e.g., through 12V connection 276. Processing system 244 can be powered by a connection 280 to power supply 272, or through one or more separate power sources, including perhaps the A/C power of the patient premises. In some embodiments, processing system 244 might have its own power supply.

Figure 2C:
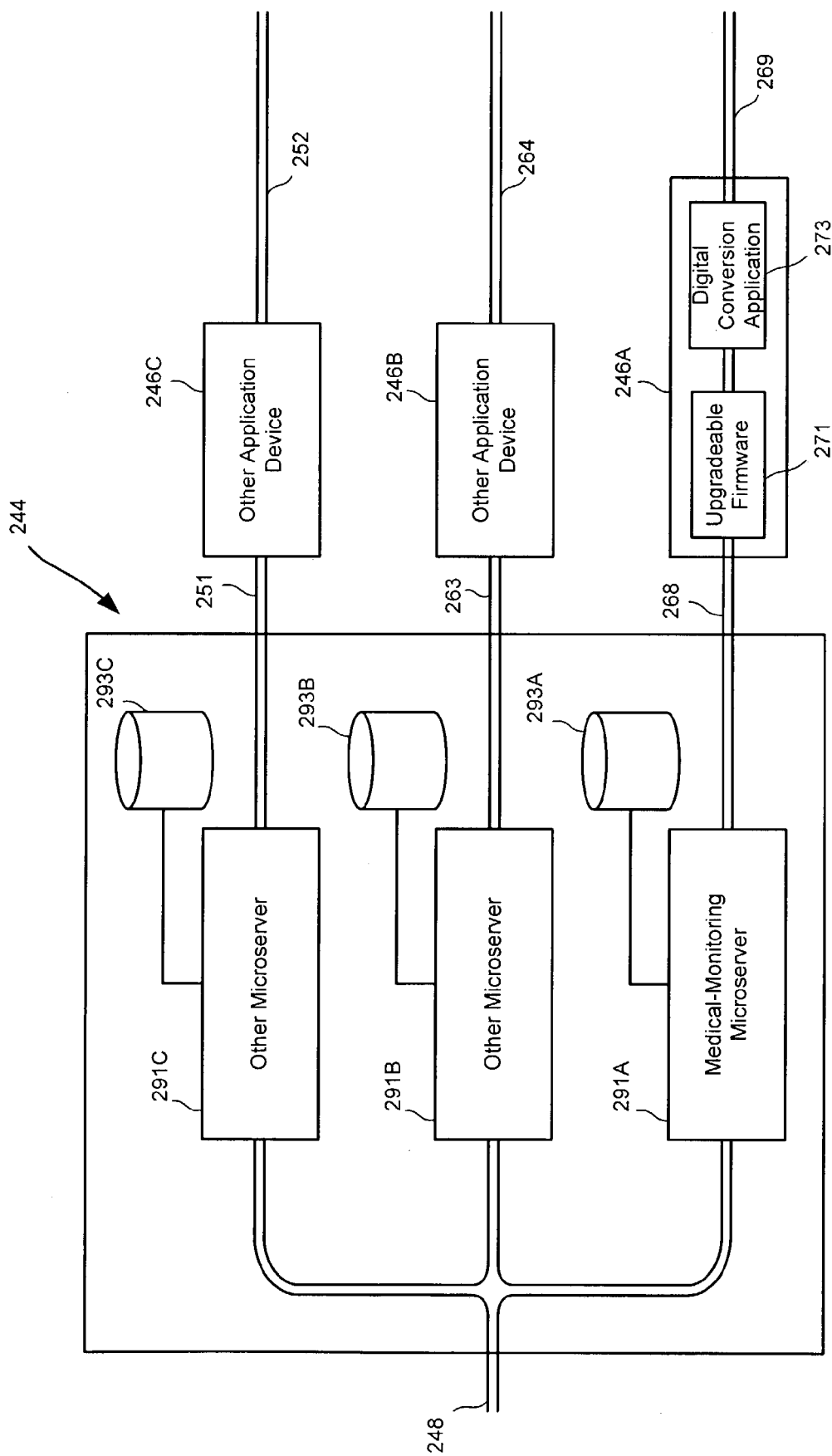

As mentioned above, processing system 244 can comprise a plurality of processing devices, and each processing device can comprise multiple components, including microservers, memory devices, storage devices and the like. As used herein, a "microserver" is intended to refer to any device programmed to perform a specified limited set of functions, such as an EPROM. Merely by way of example, FIG. 2C provides a detailed illustration of an exemplary processing system 244, which comprises multiple processing devices 291, one of which is a medical-monitoring microserver 291A adapted specifically to implement medical-monitoring functions. In accordance with the exemplified embodiment, transport medium 248 links processing system 244 with an external transport medium, perhaps via a discrimination device and/or interface, as described above.

Transport medium 248 can be coupled to a plurality of microservers 291, including the medical-monitoring microserver 291A, such that any information received by the processing system 244 via transport medium 248 may be routed to any of the microservers 291. Each microserver can, in some embodiments, be the equivalent of a server computer, complete with memory devices, storage devices, and the like, each of which is known in the art. In FIG. 2C, storage devices 293 associated with the medical-monitoring and other microservers 291 are shown. Each of the microservers may be associated with one of the application devices 246 to provide information received from transport medium 248 and specifically processed for use by the corresponding device. In particular, the medical-monitoring microserver 291A is associated with the medical-monitoring application device 246A, which is show in FIG. 2C as comprising upgradeable firmware 271 and a digital-conversion application 273. This digital-conversion application 273 is equipped to convert data collected from the patient-premises medical monitoring equipment 120A for use by the medical-monitoring microserver 291A. The firmware 271 may be configured to perform some processing of the converted data to increase its usefulness by the medical-monitoring microserver 291A.

In addition to these functions for the medical-monitoring microserver 291A, the other microservers 291 can be configured to route information sets received via transport medium 248 according to the type of information in the set (e.g., encoded video, IP data, etc.) as well as any addressing information associated with either the set or the information it comprises (e.g., a specified destination port or network address for a particular subset of information). In this way, the microservers 291 can serve switching functions somewhat similar to that described with respect to discrimination device 232 described in relation to FIG. 2A. For instance, if IP data is received by microserver 291C, such data can be routed to an Ethernet connection, to the existing telephone wiring, e.g., in an HPNA implementation, or to any other appropriate medium, perhaps via an appropriate line driver. In fact, in certain embodiments, processing system 244, and in particular one or more of microservers 291, can incorporate the functionality of discrimination device 232 and/or aggregator 240, rendering those components optional. In some embodiments, one or more of the other microservers 291B or 291C may be adapted to function as a controller for the network interface device 200, overseeing the network interface device's state and monitoring performance. In some embodiments, the controller functions can be accessed using a web browser.

Processing system 244 can have multiple means of input and output. Merely by way of example, microservers 296 can communicate with one or more external transport media (perhaps, as discussed above, via intermediary devices) using one or more transport media (e.g., 248). Processing system 244 also can communicate with one or more internal transport media via a variety of information conduits, such as category 5, 5e and/or 6 unshielded twisted pair wire 268, RG6 and/or RG59 coaxial cable 264, and category 3 unshielded twisted pair copper (telephone) wire 252, again possibly via intermediary devices, as discussed with reference to FIG. 2A. Notably, some embodiments of processing system 244 can include interfaces for multiple transport media of a particular type, for instance, if processing system 244 serves as a networking hub, switch or router. Processing system 244 can also have infra-red and radio-frequency receivers and transmitters, for instance to allow use of a remote control device, as well as wireless transceivers, for instance to allow wireless (e.g., IEEE 802.11) networking.

3. Implementation

Figure 3:
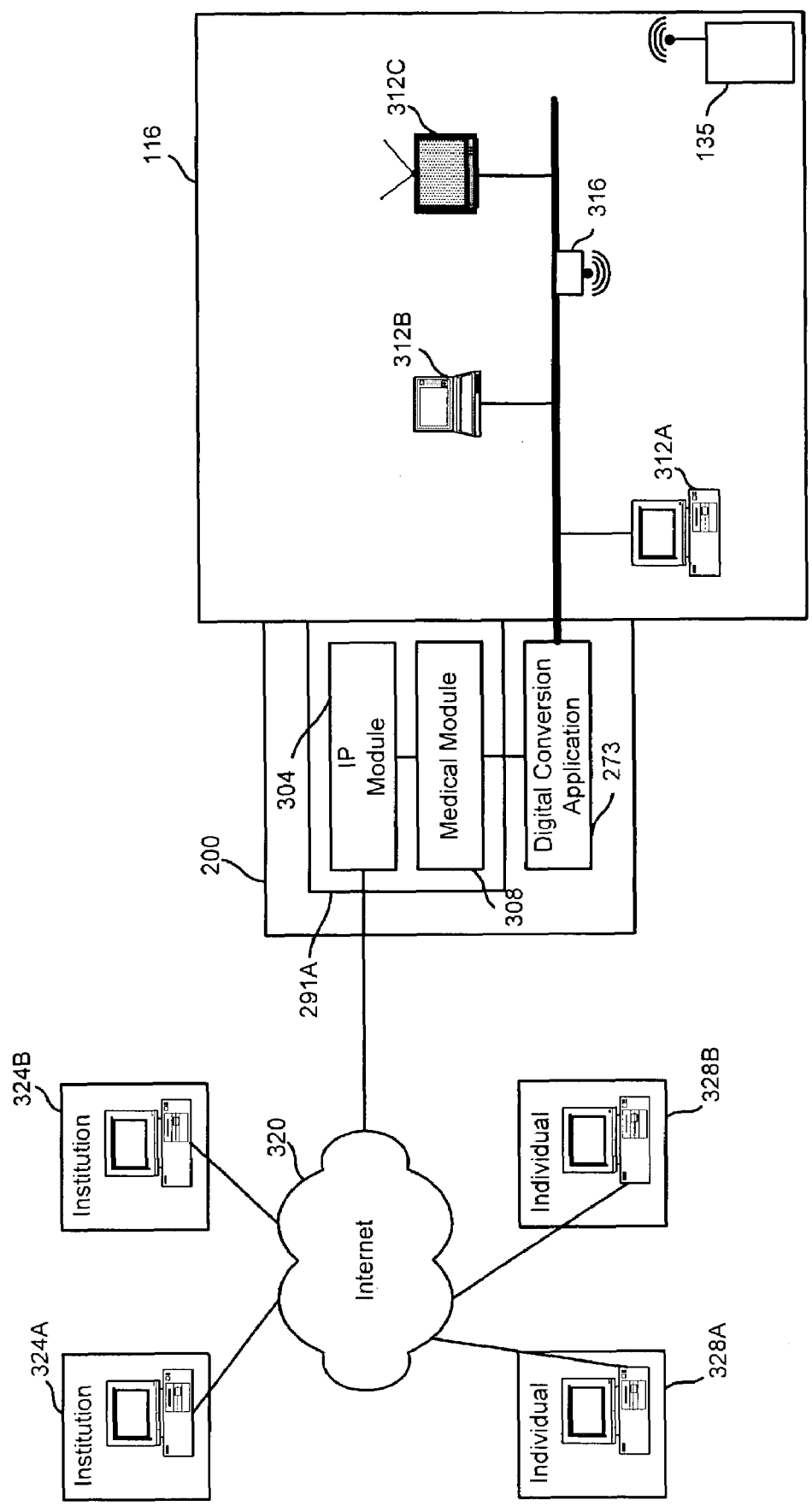
FIG. 3 provides an illustration of the use of a network interface device to provide access to medical-monitoring information from a patient premises according to embodiments of the invention.

Implementations of the medical-monitoring application with the network interface device are illustrated schematically with FIG. 3, from which various uses of the system will be evident to those of skill in the art. FIG. 3 provides a broad overview of how connections with the medical-monitoring application of the network interface device 200 may be used in implementing such medical-monitoring functions. The medical-monitoring application 291A is shown comprising an IP module 304 to permit information exchange with the Internet, and a medical module 308 that performs the diagnostic interpretive and other functions to respond to requests from the patient, detect anomalous physiological conditions, and the like.

Within the patient premises 116, the medical-monitoring functionality may use communications not only with the wireless receiver 316, adapted to receive information from the wireless transmitter 135, but may also use communications with computational devices 312A and 312B, such as personal computers, laptops, PDAs, and the like. Information relevant to medical-monitoring functions may be collected with both the wireless receiver 316 and computational devices 312. While the wireless receiver 316 permits the collection of real-time direct information from the patient, such as measured physiological information, voice information, and the like, the computational devices 312 permit collection of information that may be provided separately by the patient. For example, medical-history information could be recorded, the patient may be asked to respond to questionnaires rating subjective qualities associated with his condition or treatment, and the like. In addition, the computational devices 312 may serve as a source where the patient may receive information related to his medical monitoring, such as status reports, treatment information, and the like. In some instances, such devices may be used for on-site display of data records on a personal computer, laptop, etc. or may even simply be provided with a television 312C located on the premises.

External to the patient premises 116, relevant information may be exchanged between the network interface device 200 and individuals 328 or institutions 324 with the Internet 320. For reasons of confidentiality concerns, these individuals 328 and/or institutions 324 generally have a legitimate level of involvement with the treatment and/or medical monitoring of the patient, and security protocols may be implemented to ensure that access is limited to such individuals 328 and/or institutions 324. For example, one of the institutions 324 could be an entity responsible to monitor conditions that require an emergency response and to initiate such an emergency response. Another institution 324 could be a research institution conducting a study in which the patient is a participant, with data being collected as part of the study. Another institution 324 could be a health-care provider such as a hospital or physician's office that is monitoring recovery of the patient from a prior condition. Another institution 324 could be a health-insurance provider collecting information that it has been given permission to collect or that it is entitled to collect. The individuals 328 might include relatives or friends of the patient who are participating in decisions related to his treatment. Such a capability to provide information to such individuals may be especially useful where individuals remote from the patient premises wish to assist in treatment of the patient.

Figure 4A:
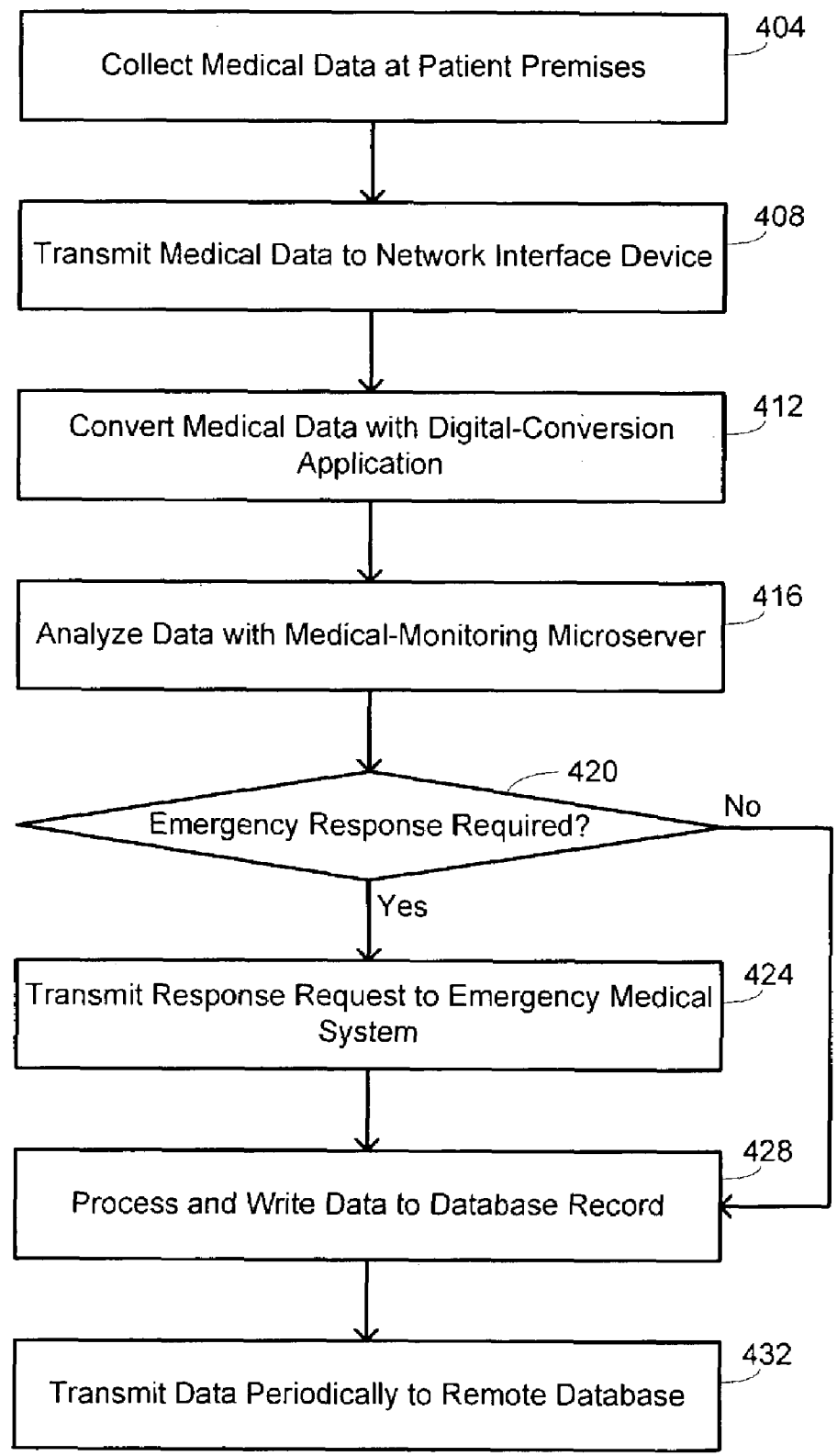
FIGS. 4A and 4B are a flow diagram illustrating methods of providing medical-monitoring services according to embodiments of the invention.
Figure 4B:
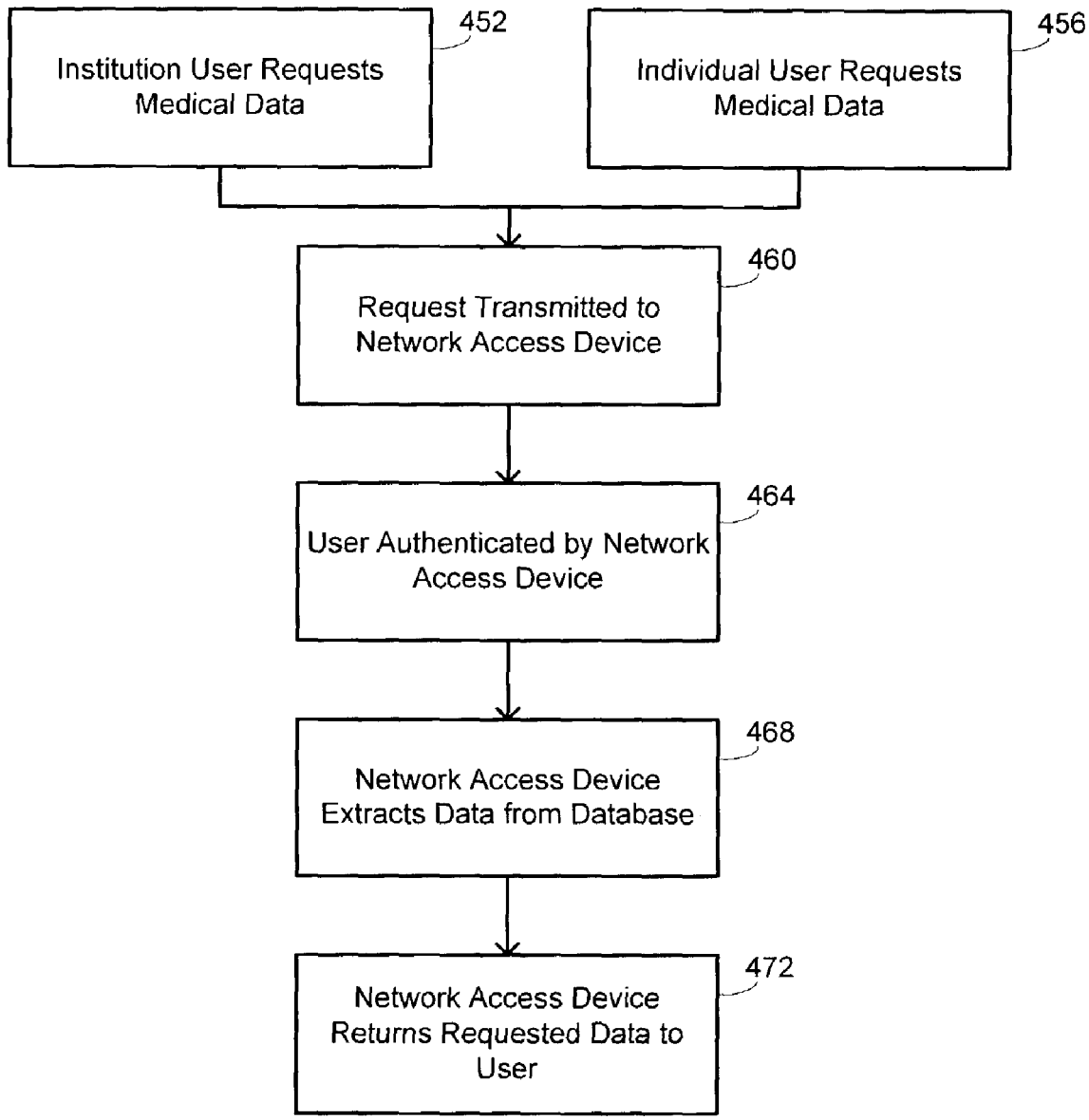

FIGS. 4A and 4B are flow diagrams that provide exemplary methods for using the medical-monitoring functions described above. FIG. 4A provides a method for monitoring medical data in which medical data are collected at the patient premises at block 404. Such medical data may broadly include physiological data collected with suitable sensors, voice data from the patient indicating a condition of the patient, a signal from a panic indicator initiated by the patient to indicate an emergency condition, and the like. The data are transmitted to the network interface device at block 408, where they may be converted with the digital-conversion application. Conversion of the data may be dependent on the type of devices to which the data are ultimately to be transmitted and the formats in which they expect to receive the data. In particular, the selected format may depend on whether the data are to intended to be processed subsequently by a human or by a machine.

Some analysis of the data may be performed with the medical-monitoring microserver in some embodiments at block 416. Such analysis may be used to determine how to direct the data, particularly in those embodiments where data may be received from multiple sources, possibly representing data for multiple patients. When data are being coordinated for multiple patients at a single location, a unique identifier may be associated with data to identify each patient uniquely. In addition, such analysis may include determining whether an emergency response is required, as indicated at block 420. The need for an emergency response may be indicated if the received data identifies that the patient has activated a panic device, if the data includes voice data indicating a need for an emergency response, if a physiological parameter has deviated from acceptable levels, etc. If an emergency response is required, a request for such a response is transmitted to an emergency medical system at block 424. Such transmission may be performed directly be the network interface device in some embodiments, although in other embodiments it will be transmitted by the medical-monitoring service provider upon receipt of an indication of the need for such a response.

At block 428, the data may be processed and written to a database record. In some instances, these data may be maintained on a database local to or comprised by the network interface device. In other instances, as indicated at block 432, the data may be transmitted to a remote database, such as one maintained by the medical-monitoring service provider.

FIG. 4B provides a method for receiving data collected during medical monitoring, such as collected with the method described in connection with FIG. 4A. A request for medical data may be made at block 452 or 456 respectively by an institution user or by an individual user. Such a request may be initiated with a web interface with fields to request either real-time or stored medical data on an identified patient. At block 460, the request is transmitted to the network access device. Authentication of the party making the request may be performed at block 464 by using digital certificates or other authentication techniques known to those of skill in the art. After authentication, the network access device extracts the requested data at block 468 and returns it to the user at block 472. The returned medical data could be stored vital-sign data or other physiological data, and may be provided in HTML, XML, or another format depending on the characteristics of the receiving system. In cases where stored data have been requested, trending data may be used to analyze patient characteristics over time.

Those of skill in the art will appreciate that while the blocks in FIGS. 4A and 4B are provided in an exemplary order, there is no requirement that respective steps be performed in the order shown. In some embodiments, the respective steps may be performed in a different order. Also, there is no requirement that all of the steps shown in FIG. 4 be performed, and in some alternative embodiments fewer or greater numbers of steps may be performed.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A system for medical monitoring of a patient at a residential patient premises, the system comprising:
   a medical-data collection device that collects medical data from the patient, wherein the medical-data collection device is interfaced with a cable or wire transport medium internal to the residential patient premises; and
   a network interface device disposed at a perimeter of the residential patient premises, the network interface device comprising:
      a plurality of application devices interfaced with the transport medium internal to the residential patient premises, wherein:
         a first of the application devices comprises a medical-monitoring application device processes the collected medical data and a second of the application devices exchanges data with a cable or wire transport medium external to the residential patient premises; and
         the transport medium internal to the residential patient premises is isolated from the transport medium external to the residential patient premises such that operational changes to one of the internal and external transport media do not affect the other of the internal and external transport media; and
      a processor in communication with the plurality of application devices and having software instructions to coordinate transmission of the collected medical data over the transport medium external to the residential patient premises.

2. The system recited in claim 1 wherein the medical-data collection device comprises:
   a first unit interfaced with the transport medium internal to the residential patient premises; and
   a second unit carried by the patient about the residential patient premises,
   wherein the first and second units support wireless communication from the second unit to the first unit.

3. The system recited in claim 2 wherein the first and second units further support wireless communication from the first unit to the second unit.

4. The system recited in claim 3 wherein the first and second units exchange of voice information.

5. The system recited in claim 2 wherein the second unit comprises a portable panic device that transmits a request for emergency assistance upon activation.

6. The system recited in claim 2 wherein the second unit measures physiological parameters of the patient.

7. The system recited in claim 1 wherein the network interface device further comprises a storage device for storing the medical data.

8. The system recited in claim 1 wherein the transport medium external to the residential patient premises comprises the Internet.

9. The system recited in claim 8 wherein the processor has software instructions to authenticate a user attempting to establish a connection with the network interface device through the Internet.

10. The system recited in claim 1 wherein a third of the application devices comprises a digital conversion application that converts the collected medical data to a desired format.

11. The system recited in claim 1 wherein a third of the application devices provides telecommunications services to the residential patient premises.

12. A method for monitoring a medical status of a patient at a residential patient premises, the method comprising:
   collecting medical data from the patient with a medical-data collection device;
   transmitting the collected medical data over a cable or wire transport medium internal to the residential patient premises from the medical-data collection device to a network interface device disposed external to the residential patient premises and at a perimeter of the residential patient premises; and
   thereafter, transmitting the collected medical data over a cable or wire transport medium external to the residential patient premises to a recipient, wherein the transport medium internal to the residential patient premises is isolated from the transport medium external to the residential patient premises such that operational changes to one of the internal and external transport media do not affect the other of the internal and external transport media.

13. The method recited in claim 12 wherein the collected medical data indicates a need for an emergency response, the method further comprising transmitting a request for the emergency response over the transport medium external to the residential patient premises.

14. The method recited in claim 13 wherein the need for the emergency response is indicated with a call for the emergency response from the patient.

15. The method recited in claim 13 wherein the need for the emergency response is indicated by a deviation of a physiological parameter measured from the patient from a defined range.

16. The method recited in claim 12 wherein the collected medical data define a physiological parameter measured from the patient.

17. The method recited in claim 12 further comprising storing the collected medical data on a storage device comprised by the network interface device.

18. The method recited in claim 12 further comprising receiving a request for the collected medical data from the recipient at the network interface device, wherein transmitting the collected medical data is performed in response to the request.

19. The method recited in claim 18 further comprising authenticating the recipient prior to transmitting the collected medical data.

20. The method recited in claim 12 further comprising digitally converting the collected medical data, wherein transmitting the collected medical data comprises transmitting the digitally converted collected medical data.

21. The method recited in claim 12 further comprising providing a telecommunications service to the residential patient premises with the network interface device.

22. A system for medical monitoring of a patient at a residential patient premises, the system comprising:
    means for collecting medical data from the patient interfaced with a cable or wire means for transporting information internal to the residential patient premises; and
    means for interfacing with a cable or wire means for transporting information external to the residential patient premises, wherein the means for interfacing is disposed at a perimeter of the residential patient premises and comprises:
        a plurality of means for supplying applications interfaced with the means for transporting information internal to the residential patient premises, wherein a first of the means for supplying applications comprises a means for processing the collected medical data and a second of the means for supplying applications exchanges information with the means for transporting information external to the residential patient premises; and
        a means for coordinating transmission of the collected medical data over the means for transporting information external to the residential patient premises,
    wherein the means for transporting information internal to the residential patient premises is isolated from the means for transporting information external to the residential patient premises such that operational changes to one of the means for transporting information internal to the residential patient premises and the means for transporting information external to the residential patient premises do not affect the other of the means for transporting information internal to the residential patient premises and the means for transporting information external to the residential patient premises.

23. The system recited in claim 22 wherein the means for collecting medical data comprises a plurality of units having means for supporting wireless communication among the plurality of units.

24. The system recited in claim 22 wherein the means for collecting medical data comprises means for receiving a call for an emergency response from the patient.

25. The system recited in claim 22 wherein the means for collecting medical data comprises means for measuring physiological parameters of the patient.

26. The system recited in claim 22 wherein the means for coordinating transmission of the collected medical data comprises means for receiving a request for transmission of the collected medical data from a recipient.

27. The system recited in claim 26 wherein the means for receiving the request comprises means for authenticating the recipient.

28. The system recited in claim 22 wherein the means for interfacing with the means for transporting information external to the residential patient premises further comprises means for storing the collected medical data.

29. The system recited in claim 22 wherein the means for interfacing with the means for transporting information external to the residential patient premises further comprises means for providing telecommunications services to the residential patient premises.

* * * * *